United States Patent [19]

Ngan

[11] Patent Number: 5,840,582
[45] Date of Patent: Nov. 24, 1998

[54] METHOD FOR DETERMINING THE HYDROGEN-TO-CARBON RATIO IN A LIQUID HYDROCARBON FRACTION AND USE THEREOF

[75] Inventor: Danny Yuk-Kwan Ngan, Houston, Tex.

[73] Assignee: Shell Oil Company, Houston, Tex.

[21] Appl. No.: 479,746

[22] Filed: Jun. 7, 1995

[51] Int. Cl.$^6$ .......................... G01N 35/08; G01N 33/22
[52] U.S. Cl. .............. 436/55; 436/60; 436/139; 436/155; 436/164; 208/46; 208/50; 208/67; 208/95; 208/100; 208/106; 250/373; 356/51; 356/70; 356/317
[58] Field of Search .................... 436/55, 60, 139, 436/141, 142, 155, 158, 164; 356/51, 70, 317, 318; 250/373; 201/1, 31; 208/46, 50, 52 R, 67, 72, 95, 100, 106

[56] References Cited

U.S. PATENT DOCUMENTS

| | | | |
|---|---|---|---|
| 2,822,475 | 2/1958 | Miller | 250/372 |
| 2,847,578 | 8/1958 | Staten, Jr. | 250/372 |
| 4,388,408 | 6/1983 | Sien et al. | 436/60 |
| 4,556,326 | 12/1985 | Kitchen, III et al. | 436/155 X |
| 4,783,416 | 11/1988 | Patel | 436/60 |

OTHER PUBLICATIONS

B.P. Ennis et al; "High Temperature–Low Contact Time Pyrolysis Process", Symposium Series 43, Institute of Chemical Engineers, Harrogate, Eng., Jun. 1975.

Kirk–Othmer Encyclopedia of Chemical Technology, 3rd Ed., vol. 9, pp. 400–411.

Primary Examiner—Jill Warden
Assistant Examiner—Maureen M. Wallenhorst

[57] ABSTRACT

In a first embodiment of the invention, a method for determining the hydrogen-to-carbon ratio of a liquid hydrocarbon fraction is presented. A sample of the liquid fraction is subjected to an ultra-violet absorption analysis. The results of the analysis correlate directly to the hydrogen-to-carbon ratio of the hydrocarbon fraction and, with a knowledge of this correlation, the hydrogen-to-carbon ratio of the sample under analysis may be determined. Another embodiment provides a method for monitoring the performance of a process for the preparation of olefins by the thermal cracking of a hydrocarbon feedstock. A liquid fraction is recovered from the product of the thermal cracking and subjected to an ultra-violet absorption analysis. The result of the analysis correlates directly to the hydrogen-to-carbon ratio of the product, which in turn correlates to the cracking severity being applied in the thermal cracking process. Thus, the analytical result may by employed in a system to control the thermal cracking process. Further, when the result of the analysis is corrected for the nature of the hydrocarbon feedstock and the yield of the liquid fraction, the result correlates directly to the rate of formation of quench exchanger coke in the thermal cracking process. The corrected result may thus be used to monitor and control the coking rate.

16 Claims, 2 Drawing Sheets

5,840,582

METHOD FOR DETERMINING THE HYDROGEN-TO-CARBON RATIO IN A LIQUID HYDROCARBON FRACTION AND USE THEREOF

FIELD OF THE INVENTION

The present invention relates to a method for determining by analysis the hydrogen-to-carbon ratio in a liquid hydrocarbon fraction and to the use of the method in monitoring and controlling a hydrocarbon thermal cracking process, in particular a thermal cracking process preparing lower olefins.

BACKGROUND OF THE INVENTION

A number of processes for the refining and processing of hydrocarbons require knowledge of ratio of hydrogen-to-carbon in either the hydrocarbons being processed and/or produced. One such process is the preparation of olefins, in particular lower olefins, by the thermal cracking of hydrocarbon feedstocks.

The thermal cracking, or pyrolysis, of a hydrocarbon feedstock to prepare olefins is a well known technique in the art. The process is operated on a commercial scale to produce olefins, for example ethylene and propylene, in large quantities. A common process for commercial application is one in which the hydrocarbon feedstock is passed through one or more tubes or coils which are heated externally by means of burners. The properties of the hydrocarbon feedstock and the conditions under which the thermal cracking takes place determine the nature and contents of the product. In general, it is desirable to operate the thermal cracking process so as to minimize the degree of coking and the production of methane. The depth of cracking or degree of conversion in the thermal cracking process is referred to as the cracking severity. The level of coking and methane production generally increase as the severity of the thermal cracking increases, until a point is reached at which the level of coke and methane formation becomes unacceptable. This point is often referred to as the maximum cracking severity, and represents an optimum point combining a high olefin yield with an acceptable length of time for which the process may be operated before the build up of coke requires the process plant to be shut down.

It follows that, for the production of olefins on a commercial scale, it is highly desirable to be able to operate the thermal cracking process at or as close as possible to the maximum cracking severity. A number of indicators of cracking severity have been determined for use in controlling commercial thermal cracking processes. Examples of such indicators include the cracking severity index, of use in naphtha cracking, and the molecular collision parameter, used in the thermal cracking of gasoil. Other indicators include the outlet temperature of the thermal cracking tube or coil, and the hydrogen content of the liquid products of the cracking process. A parameter commonly employed in the manufacture of ethylene is the propylene-to-methane ratio (PMR) or the ethylene-to-methane ratio (EMR) of the gaseous product of the thermal cracking process. However, the sensitivity of these indicators to factors such as changes in the hydrocarbon feedstock and to the reliability of the product sampling techniques give rise to problems when using these indicators as part of a thermal cracking process control system.

Accordingly, there is a need for an indicator of cracking severity which is not sensitive to such process parameters as feedstock fluctuations and which may be readily incorporated into a process control system. B. P. Ennis et al ("High Temperature—Low Contact Time Pyrolysis Process", Symposium Series 43, Institute of Chemical Engineers, Harrogate, Eng., June 1975) describe a steam pyrolysis process for the thermal cracking of a wide range of naphtha fractions. Ennis et al state that a particularly valuable index of pyrolysis severity is the hydrogen-to-carbon atomic ratio in the pyrolysis gasoline product or $C_5$ and heavier ($C_5+$) products. Ennis et al describe this as being a measure of the degree of dehydrogenation of the liquid phase and the resulting tendency for coke formation. Since the calculated hydrogen-to-carbon ratio of the $C_5+$ products depends only on the predicted yield of $C_4$ and lighter components and the hydrogen-to-carbon ratio of the feed, Ennis et al claim that this severity indicator is an excellent means of comparing selectivity at the same depth of cracking for various pyrolysis reactors or feedstocks.

While Ennis et al suggest the use of hydrogen-to-carbon ratio of the $C_5+$ products to be a useful indicator of cracking severity, there is no disclosure made of how this parameter is to be measured or how it may be used to control a thermal cracking process on a commercial scale. Heretofore, the ratio of hydrogen-to-carbon in the liquid ($C_5+$) hydrocarbon product of a thermal cracking process has been difficult to determine. Typically, in a commercial thermal cracking process, it is calculated on the basis of an analysis of the hydrocarbon feedstock and the gaseous ($C_4-$) products, usually obtained after a detailed feed characterization followed by a simulation of the cracking conditions using a model. However, none of the options available are practical if the hydrogen-to-carbon ratio is to be used as a control parameter.

Accordingly, there is a need for a method of determining the hydrogen-to-carbon ratio of a liquid hydrocarbon fraction which may be readily incorporated in commercial process control scheme.

It has now been found that an indication of the hydrogen-to-carbon ratio of a liquid hydrocarbon fraction, for example the $C_5+$ products of a thermal cracking process, may be obtained by subjecting the fraction to an analysis using ultra-violet absorption techniques. This analysis may be carried out on-line and the results used directly in a process control system, for example to monitor and/or control the thermal cracking process described above.

SUMMARY OF THE INVENTION

The present invention provides a method for determining the hydrogen-to-carbon ratio of a liquid hydrocarbon fraction, which method comprises subjecting a sample of the liquid fraction to an ultra-violet absorption analysis. The results of the analysis correlate directly to the hydrogen-to-carbon ratio of the hydrocarbon fraction. Thus, given a knowledge of the correlation between the ultra-violet absorbance of a liquid hydrocarbon fraction and its hydrogen-to-carbon ratio, the hydrogen-to-carbon ratio of the sample under analysis may be determined.

In a further aspect, the invention provides a method for monitoring the performance of a process for the preparation of olefins by the thermal cracking of a hydrocarbon feedstock, which method comprises recovering a liquid fraction from the product of the thermal cracking and subjecting a sample of the fraction to an ultra-violet absorption analysis. The result of the analysis correlates directly to the hydrogen-to-carbon ratio of the product, which in turn correlates to the cracking severity being applied in the thermal cracking process. This allows the analytical result to be employed in a system to control the thermal cracking process. Further, when the result of the analysis is corrected for the nature of the hydrocarbon feedstock and the yield of the liquid fraction, the result correlates directly to the rate of formation of coke in the thermal cracking process. The corrected result may thus be used to monitor and control the quench coking rate.

THE DRAWINGS

FIG. 1 is a schematic representation of a process scheme of one embodiment of the present invention, in which the cracking severity of a thermal cracking unit is monitored and controlled; and FIG. 2 is a schematic representation of a process scheme of a further embodiment of the present invention, in which the coking rate of a thermal cracking unit is monitored.

DESCRIPTION OF THE PREFERRED EMBODIMENTS

Figure 1:
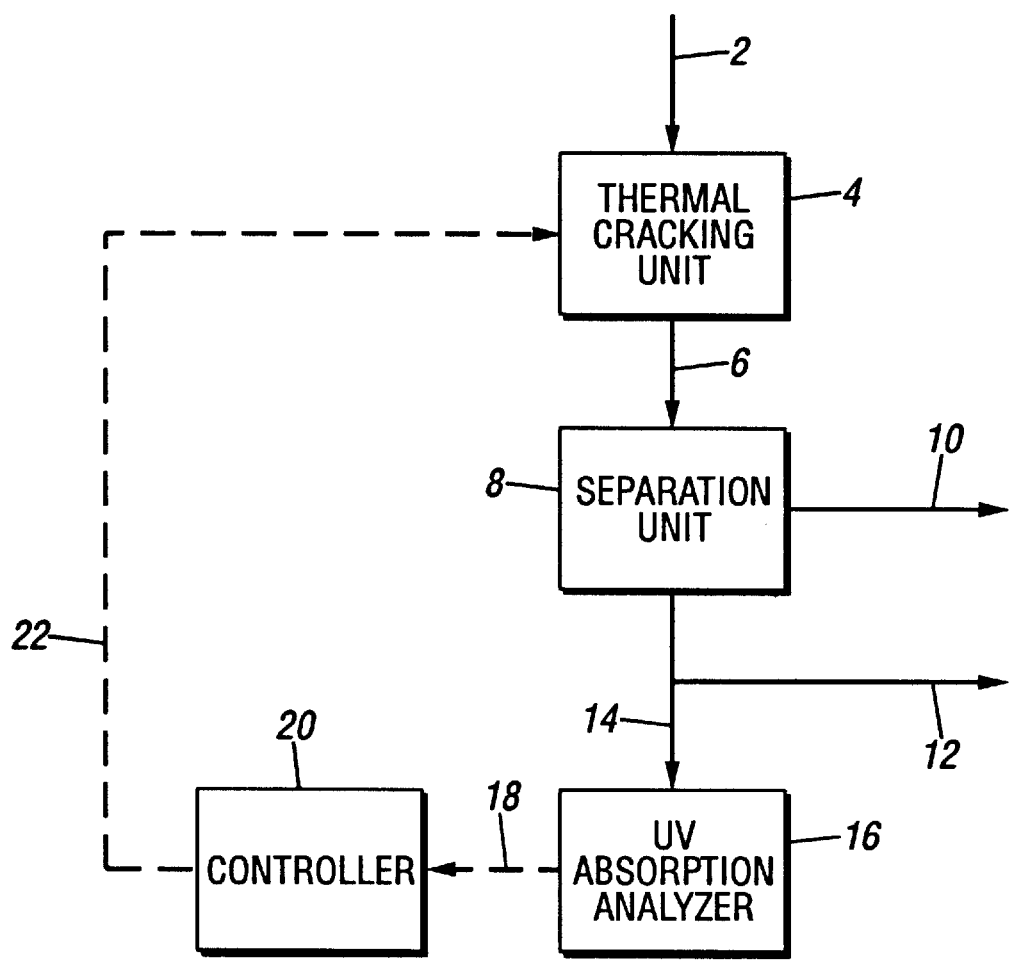

In a first aspect, the present invention provides a method for determining the hydrogen-to-carbon ratio of a liquid hydrocarbon fraction, which method comprises subjecting a sample of the liquid fraction to an ultra-violet absorption analysis. For the avoidance of doubt, the term "hydrogen-to-carbon ratio" as used herein is a reference to the ratio of hydrogen moieties to carbon moieties in the hydrocarbon molecules present in the products.

A sample of the liquid hydrocarbon fraction is removed and placed in a suitable container. The container is transparent to ultra-violet light, at least to the wavelength at which the absorbance is being determined. The sample may be diluted if required. Suitable diluents include organic solvents, such as alcohols and aromatic solvents, for example toluene. The container and the fraction sample are irradiated with ultra-violet light. The sample is preferably analyzed to determine the absorption of ultra-violet light at the wavelength of 310 nm and greater, more preferably in the range of from 310 to 550 nm. The intensity of the ultra-violet light passing through and leaving the sample and container is measured. The intensity of the light leaving the sample will be lower than the intensity of the light leaving the source, due to the absorption by hydrocarbon molecules in the liquid hydrocarbon fraction of the ultra-violet light. It has been found that, for a given intensity of the source of the ultra-violet light, the intensity of the ultra-violet light leaving the sample may be correlated to the hydrogen-to-carbon ratio of the hydrocarbons in the liquid hydrocarbon fraction. By employing a suitable detector, the analytical result, that is the intensity of the ultra-violet light leaving the sample, may be converted into a process signal for use in a process control system. A correction may be required in processing the analytical result in those cases in which the liquid hydrocarbon sample is diluted prior to analysis.

By determining the correlation between the ultra-violet absorbance of a range of similar hydrocarbon fractions and the hydrogen-to-carbon ratio of the fractions, the results of an ultra-violet absorbance analysis, carried out for example on-line in a hydrocarbon processing plant, may be used to provide an indication of the hydrogen-to-carbon ratio of the sample. The results of the analysis may then be used to control the process. One suitable application of this technique is in the analysis and control of the liquid products of a hydrocarbon thermal cracking process, as used in the manufacture of olefins, particularly lower olefins such as ethylene and propylene.

In a further aspect, the present invention provides a process for the preparation of olefins, in particular lower olefins such as ethylene and propylene, by the thermal cracking of a hydrocarbon feedstock, which process comprises the steps of (a) feeding the hydrocarbon feedstock to a thermal cracking zone and subjecting the hydrocarbon feedstock to operating conditions under which at least a portion of the hydrocarbon feedstock is thermally cracked, thereby yielding a cracking product;

(b) recovering from the cracking product a liquid hydrocarbon fraction;

(c) subjecting the liquid hydrocarbon fraction to an analysis in which the ultraviolet absorbance of the liquid hydrocarbon fraction is determined yielding an analytical result;

(d) comparing the analytical result with a predetermined desired analytical result correlating to a desired hydrogen-to-carbon ratio in the liquid hydrocarbon fraction; and (e) adjusting the operating conditions of the cracking zone to obtain the desired analytical result.

The hydrocarbon feedstock used in the thermal cracking process of the present invention may be any of the hydrocarbons or hydrocarbon fractions used in conventional thermal cracking processes for the preparation of olefins. Suitable feedstocks range from $C_4$ fractions, such as butane, $C_5$ fractions, such as pentane, as well as gasoline, naphtha, kerosine and gasoil fractions. Hydrocarbon feedstocks as heavy as vacuum gasoils may also be employed. The process of the present invention is particularly suitable for use with gasoline, naphtha, kerosine and heavy gasoil fractions, with gasoline and naphtha fractions being especially preferred feedstocks. The hydrocarbon feedstocks are readily produced, for example, by means of the conventional refining of crude oil. The hydrocarbon feedstock may consist of a single fraction mentioned hereinbefore or a mixture of the fractions. It is an advantage of the process of this invention that fluctuations in the composition and boiling point range of the hydrocarbon feedstock may occur and be accommodated by the control system. That is, the use of the ultra-violet analysis to obtain an analytical result correlating to a given hydrogen-to-carbon ratio in the liquid hydrocarbon fraction of the product is not sensitive to fluctuations or changes in the composition or boiling point range of the hydrocarbon feedstock.

The hydrocarbon feedstock is subjected to thermal cracking in a thermal cracking zone. Any suitable process arrangement and apparatus may be employed for the purposes of the present invention. A process regime commonly applied on a commercial scale employs tubular reactor coils installed in externally fired heaters. The hydrocarbon feedstock is fed to the tubular reactor coils which, when heated form the thermal cracking zone. Heating of the coils is typically effected by the combustion of a suitable fuel, such as a hydrocarbon oil or refinery gas. Suitable apparatus for carrying out the thermal cracking are well known in the art. For a general discussion of aspects of the thermal cracking of hydrocarbon feedstocks to yield olefins, reference is made to *Kirk-Othmer Encyclopedia of Chemical Technology*, Third Edition, Volume 9, pages 400 to 411.

The operating conditions of the thermal cracking zone are dependent upon the specific design of the thermal cracking apparatus and the severity of cracking required. The hydrocarbon feedstock is heated in the thermal cracking zone until a temperature is reached at which the hydrocarbon molecules crack. The temperature required to effect cracking will depend upon the composition and boiling point range of the feedstock. Typical temperatures for the thermal cracking, measured at the outlet of the thermal cracking zone, are in the range of from 750° C. to 950° C., more preferably from 800° C. to 900° C.

The process may be operated at any suitable pressure. The thermal cracking is preferably carried out at a pressure, measured at the outlet of the thermal cracking zone, in the range of from 1 to 5 bar, more preferably from 1 to 3 bar.

The flowrate at which the hydrocarbon feedstock is supplied to the thermal cracking zone will depend upon the specific design of the process apparatus. Within these constraints, any suitable flowrate may be employed. Typically, the flowrate of the hydrocarbon feedstock is in the range of from 10,000 kg/hr to 40,000 kg/hr, more preferably from 15,000 kg/hr to 30,000 kg/hr.

The residence time of the hydrocarbon feedstock in the thermal cracking zone will depend upon the apparatus design and the other process operating conditions. Typical residence times for the hydrocarbon feedstock in the thermal cracking zone are in the range of from 0.1 to 1.0 seconds, more preferably from 0.15 to 0.75 seconds.

To aid the thermal cracking process, the hydrocarbon feedstock may be mixed with an inert diluent and the resulting mixture fed to the thermal cracking zone. A most suitable inert diluent is steam. The inert diluent is typically present in a weight ratio of diluent-to-hydrocarbon of from 0.1 to 1.0 kg/kg, more preferably from 0.3 to 0.7 kg/kg.

The effluent leaving the thermal cracking zone of the process comprises a range of components in both the liquid and gas phases. The gas phase comprises methane and lower olefins, in particular ethylene and propylene, together with other $C_3$ and some $C_4$ hydrocarbons. The liquid phase consists substantially of $C_5$ and higher hydrocarbons. Separation of the effluent in order to recover the desired olefin products is typically carried out using a combination of compression, condensation and fractionation. Techniques for the separation are well known and established in the art. In this respect, reference is again made to *Kirk-Othmer Encyclopedia of Chemical Technology,* Third Edition, Volume 9, pages 400 to 411.

For the purposes of the present invention, it is necessary to recover from the effluent of the thermal cracking zone the liquid hydrocarbon fraction. The $C_5+$ hydrocarbons present in the effluent will make up the liquid fraction. A sample of this fraction is subjected to an ultra-violet analysis, the results of which are used to control the severity of the cracking of the hydrocarbon feedstock occurring in the thermal cracking zone. The sample may be of the entire $C_5$ + liquid fraction. Alternatively, a narrower liquid fraction, for example that fraction boiling above about 230° C. or that fraction boiling above about 320° C., may be equally well employed.

In a further aspect of the present invention, there is provided a method for controlling a process for the thermal cracking of a hydrocarbon feedstock in a thermal cracking zone, which method comprises recovering a sample of a liquid hydrocarbon fraction of a cracking product obtained from the thermal cracking of a hydrocarbon feedstock in the thermal cracking zone; subjecting the sample to an analysis in which the ultra-violet absorbance of the sample is determined yielding an analytical result which may be correlated to the hydrogen-to-carbon ratio of the liquid hydrocarbon fraction; comparing the analytical result with a predetermined desired analytical result correlating to a desired hydrogen-to-carbon ratio in the liquid hydrocarbon fraction; and adjusting the operating conditions of the cracking zone to obtain the desired analytical result.

The process control system retains a value for an analytical result corresponding to a given, predetermined hydrogen-to-carbon ratio of the hydrocarbons in the liquid hydrocarbon fraction, which ratio in turn has been correlated to a desired level of cracking severity. The result generated as a result of the analysis of the liquid hydrocarbon fraction is compared with the result corresponding to the predetermined hydrogen-to-carbon ratio. The cracking severity of the thermal cracking zone is then adjusted to produce a liquid hydrocarbon fraction which, upon analysis, exhibits an ultra-violet absorbance yielding an analytical result acceptably close to the desired result. The cracking severity may be altered by varying one or more of the process operating parameters of the thermal cracking zone, for example the temperature, pressure, residence time and/or the flowrate of the hydrocarbon feedstock.

The hydrogen-to-carbon ratio in the liquid hydrocarbon fraction of the effluent of the thermal cracking zone decreases as the cracking severity in the thermal cracking zone increases. The thermal cracking process is preferably operated to yield a liquid hydrocarbon fraction in the effluent having a hydrogen-to-carbon ratio of greater than 1.0. The hydrogen-to-carbon ratio is preferably about 1.1.

The results of the analysis may be used to compare with the predetermined desired analytical result in order to make the necessary alterations in the operating conditions of the thermal cracking zone. However, as the analytical result is correlated to the cracking severity being achieved, it may be desirable to use the result to give an indication of the cracking severity to assist in operating the process.

Surprisingly, it has been found that, with some correction for the nature of the hydrocarbon feedstock and the yield of liquid hydrocarbons, the ultra-violet analysis of the liquid hydrocarbon fraction of the product may be directly correlated to the coking rate occurring in quench exchanger downstream of the thermal cracking unit. The quench coking rate is the rate at which coke is forming and building up on the internal surfaces of the quench exchangers downstream of the thermal cracking unit.

Accordingly, in a further aspect, the present invention provides a method for monitoring the coking rate in a process for the preparation of olefins by the thermal cracking of a hydrocarbon feedstock, which method comprises the steps of:

(a) feeding the hydrocarbon feedstock to a thermal cracking zone and subjecting the hydrocarbon feedstock to operating conditions under which at least a portion of the hydrocarbon feedstock is thermally cracked, thereby yielding a cracking product;

(b) recovering from the cracking product a liquid hydrocarbon fraction;

(c) subjecting a sample of the liquid hydrocarbon fraction to an analysis in which the ultra-violet absorbance of the liquid hydrocarbon fraction is determined yielding an analytical result;

(d) correcting the analytical result for the effects of the hydrocarbon feedstock and the yield of liquid hydrocarbons to yield a corrected analytical result; and (e) determining the coking rate from the corrected analytical result.

The analytical result may be corrected for the effects of the hydrocarbon feedstock by subjecting the feedstock to an ultra-violet absorption analysis as described hereinbefore in relation to the product of the thermal cracking process. The result obtained from the analysis of the feedstock may be used, together with the yield of the liquid hydrocarbon fraction obtained, to provide a corrected analytical result for the thermal cracking effluent. Once the correlation between the corrected result of the ultra-violet absorption analysis has been determined, this correlation may be incorporated in the control allowing the results of an on-line ultra-violet analysis to be readily converted into a reading for the coking rate. The process operating conditions may be adjusted accordingly, to control the coking rate.

Embodiments of the present invention will be described with reference to the accompanying Figures, which are schematic representations of process schemes for a thermal cracking process according to embodiments of the present invention.

Referring to FIG. 1, a hydrocarbon feedstock is fed via line 2 to a thermal cracking unit 4. The effluent from the thermal cracking unit 4, comprising unconverted feedstock, liquid and gaseous products, is fed via line 6 to a separation unit 8, in which the liquid fraction (consisting mainly of $C_5+$ hydrocarbons) and the gaseous fraction (comprising $C_4-$ hydrocarbons, hydrogen and any inert diluent, such as steam, present in the feed) are separated. The gaseous fraction is recovered from the process via line 10 to be fed to further separation and refining stages (not shown). The liquid fraction is removed from the separation unit via line 12 to be led to further separation and refining operations (not shown). Unconverted hydrocarbon feedstock may be recycled to the thermal cracking unit 4 (recycle not shown).

A sample of the liquid fraction is removed from line 12 via line 14 and fed to an ultra-violet absorption analyzer 16. In the analyzer 16 the sample is subjected to an analysis as described hereinbefore to determine the ultra-violet absorbance of the liquid hydrocarbon fraction. The result of the analysis is transmitted via a control line 18 to a controller 20, in which the result of the analysis is compared with a preset result corresponding to a desired cracking severity occurring in the thermal cracking unit 4. Should the controller 20 detect a difference between the actual result of the analysis and the preset result, the controller 20 will alter one or more of the operating conditions of the thermal cracking unit 4, thereby adjusting the cracking severity. The means linking the controller 20 with the thermal cracking unit 4 for controlling the operating conditions are shown generally in the Figure as 22.

The cracking severity of the thermal cracking unit may be controlled by adjusting the preset result stored in the controller 20, against which the analytical result is compared.

Figure 2:
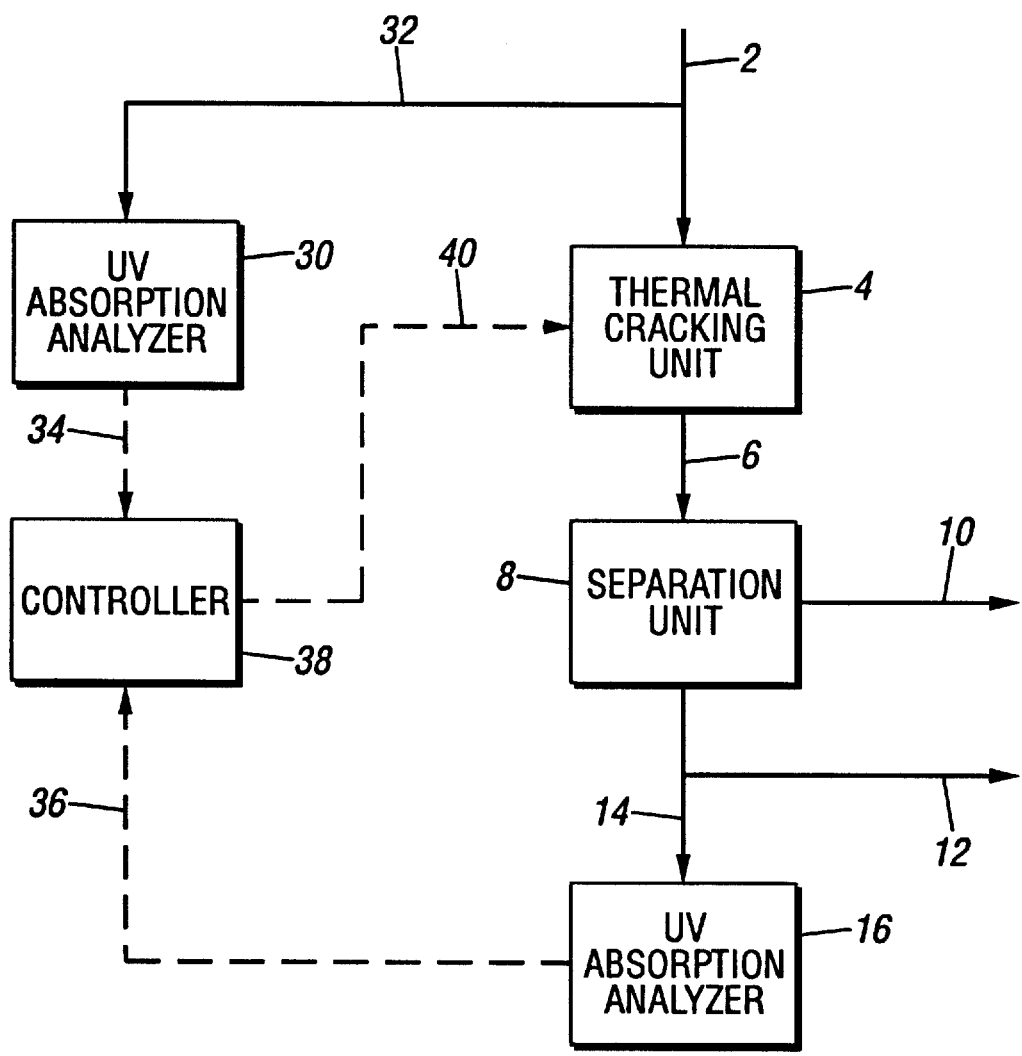

Referring to FIG. 2, a thermal cracking process scheme is shown. The parts of FIG. 2 identical to those of FIG. 1 are indicated by the same reference numerals described above. A sample of the liquid hydrocarbon product of the thermal cracking unit is analyzed in the ultra-violet analyzer 16. A similar analyzer 30 receives a sample of the hydrocarbon feedstock from line 2 via line 32. The results of the analyses of the hydrocarbon feedstock and the liquid hydrocarbon fraction are transmitted via control lines 34 and 36 respectively to a controller 38. The yield of the liquid hydrocarbon product may be obtained, for example, by measuring the flowrate of liquid fraction in line 12 (means for which are not shown). The controller 38 corrects the analytical result obtained from the ultra-violet analysis of the liquid fraction of the thermal cracking product using the result of the analysis of the hydrocarbon feedstock (received via control line 34) and the yield of the hydrocarbon liquid product. The corrected result may be used to control the operating conditions of the thermal cracking unit 4 (generally indicated by control line 40). The corrected result may also be used to provide indication of the coking rate, to aid in the overall process operation.

The present invention is further illustrated by means of the following examples. It is to be understood that the examples are embodiments only and are given the purpose of illustration and the invention is not to be regarded as limited to any specific components and/or specific conditions recited therein.

EXAMPLE 1

Hydrocarbon Feedstock Analysis

A range of hydrocarbon feedstocks were selected as follows:

Feed A: Isthmus Maya Heavy Gasoil

Feed B: Straight Run Heavy Gasoil

Feed C: Straight Run Light Iranian Blend of Heavy Gasoil and Extra Heavy Gasoil in a weight ratio of 80/20

Feed D: Hydrotreated Feed D

Feed E: Feed D hydrocracked (26.8% conversion to hydrocarbons boiling below 190° C. (375° F.))

Feed F: Blend of Feed E and hydrocracked Feed C (44.8% conversion to hydrocarbons boiling below 190° C. (375° F.)) (74.7/25.3 by weight)

Feed G: Selective Hydrocracker Bottoms

Feed H: Straight Run Heavy Gasoil

Feed I: Feed C hydrocracked (44.8% conversion to hydrocarbons boiling below 190° C. (375° F.)) (74.7/25.3 by weight)

Feed J: Blend of Feed C and Catalytically Cracked Light Gasoil (73.1/26.9 by weight), hydrocracked (26.6% conversion to hydrocarbons boiling below 190° C. (375° F.)).

Each hydrocarbon feedstock was analyzed using gravimetric determination to ascertain its carbon and hydrogen content in weight percent, from which its hydrogen-to-carbon molar ratio was calculated.

A sample of each hydrocarbon feedstock was analyzed to determine its ultra-violet absorbance using the following general procedure, to give an analytical result (hereafter indicated as "$UV_{feed}$").

The sample was diluted with toluene and placed in an ultra-violet transparent cell. The cell was irradiated with ultra-violet light and the absorption of the ultra-violet light in the wavelength range of from 310 to 400 nm measured. The integral of the ultra-violet absorbance curve between 310 and 400 nm was taken to give an analytical result.

The results of the analysis are set out in Table I.

An analysis of the data set out in Table I shows that a correlation exists between $UV_{feed}$ and the hydrogen-to-carbon ratio of the hydrocarbon feedstocks tested. For the feedstocks, ln $UV_{feed}$ and the hydrogen-to-carbon ratio are related by the following straight line relationship:

$$\ln UV_{prod} = P + Q \text{ (hydrogen-to-carbon ratio)}$$

in which P and Q are constants having values of 47.87 and −24.78 respectively.

TABLE I

| Feed | H-to-C ratio of feed | $UV_{feed}$ |
|---|---|---|
| A | 1.86 | 7.31 |
| B | 1.86 | 7.48 |
| C | 1.86 | 10.10 |

TABLE I-continued

| Feed | H-to-C ratio of feed | $UV_{feed}$ |
|------|---------------------|-------------|
| D | 1.91 | 1.97 |
| E | 1.99 | 0.33 |
| F | 1.92 | 1.27 |
| G | 1.94 | 0.61 |
| H | 1.82 | 12.33 |
| I | 2.00 | 0.38 |
| J | 1.95 | 0.15 |

EXAMPLE 2

Ultra-Violet Analysis of Thermal Cracking Liquid Product

Each of the hydrocarbon feedstocks described in Example 1 was subjected to a thermal cracking operation using the following general experimental procedure:

The hydrocarbon feedstock was mixed with steam (steam-to-hydrocarbon weight ratio of 0.5 to 0.6) and fed to a tubular coil of a thermal cracking unit comprising a preheat zone and three radiant zones, the hydrocarbon running through each of the preheat zones and radiant zones in turn. The thermal cracking unit was generated to have a coil outlet temperature of from about 800° to 850° C. and a coil outlet pressure of about 2 to 2.7 bar. The hydrocarbon feedrate was from 3 to 3.5 kg/hr. The hydrocarbon had a residence time in the coil of 0.3 seconds.

The effluent from the thermal cracking unit, containing the cracking product, uncracked hydrocarbon feedstock and steam, was led to a quench pot and quenched, yielding a gas fraction and a liquid hydrocarbon fraction.

The liquid hydrocarbon fraction was recovered from the quench pot. A sample of the liquid hydrocarbon fraction was analyzed to determine its ultra-violet absorbance using the general procedure described in Example 1 above, giving an analytical result (hereafter indicated as "$UV_{prod}$").

A sample of the liquid hydrocarbon product was analyzed using the general procedure set out in Example 1 above to determine the hydrogen and carbon content, and hence the hydrogen-to-carbon ratio, of the liquid product.

The yield of the liquid fraction recovered was determined and is hereafter indicated as $Y_{liq}$ (weight of hydrocarbon liquid product/weight of hydrocarbon feedstock). A corrected ultra-violet absorbance result for the hydrocarbon liquid product (hereafter indicated as "$UV_{corr}$") was calculated using the following relation:

$$UV_{corr} = UV_{feed} + Y_{liq}(UV_{prod} - UV_{feed})$$

The quench coking rate was determined using the following general procedure:

To determine the quench coking rate, a concentric tube-in-tube heat exchanger was placed in line between the outlet of the thermal cracking unit and the quench pot. The effluent from the thermal cracking unit was fed to the inner tube of the heat exchanger. Preheated nitrogen was fed to the annulus between the inner and outer tubes of the heat exchanger flowing counter-currently to the effluent flow. The flowrate of the nitrogen was adjusted to achieve an approximately constant temperature difference along the exchanger of from about 45° to 65° C. between the effluent and the nitrogen. The heat exchanger was operated under conditions allowing coke to form in the inner tube, with near-plug flow conditions at the tube outlet.

After being allowed to reach steady state operation, the thermal cracking unit and heat exchanger were operated for 12 hours. Operating conditions for the thermal cracking unit were as described above. The apparatus was allowed to cool to ambient temperature. The profile of the coke deposition was determined by removing the fittings from the inner tube of the heat exchanger and reaming out and collecting the coke using a drill bit. The coking rate (in mm/day) was calculated from the amount of coke removed.

The characteristics of each of the above hydrocarbon feedstocks are set out in Table I above. The results of the thermal cracking experiments for each of the above feedstocks are set out in Table II below.

From the data contained in Table II, it can be seen that the value of $UV_{prod}$ correlates very closely to the hydrogen-to-carbon ratio of the liquid hydrocarbon fraction yielded in each case. The correlation is in the form of a straight line relationship and may be expressed in the following terms:

$$ln\ UV_{prod} = P + Q \text{ (hydrogen-to-carbon ratio)}$$

in which P and Q are both constants. For the range of hydrocarbon feedstocks tested, P is 9.397 and Q is −3.07.

Further, the data set out in Tables I and II show that $UV_{corr}$ correlates very closely to the coking rate (expressed in mm/day). The correlation may be expressed as follows:

$$ln(\text{coking rate}) = R + S(ln\ UV_{corr})$$

which R and S are both constants. For the hydrocarbon feedstocks tested, R is −35.42 and S is 6.09.

TABLE II

| Feed | H-to-C ratio of liquid product | $UV_{prod}$ | $Y_{liq}$ | $UV_{corr}$ | Coking Rate (mm/day) |
|------|-------------------------------|-------------|-----------|-------------|----------------------|
| A | 0.89 | 813.81 | 0.43 | 354.35 | 2.10 |
|   | 0.93 | 613.60 | 0.42 | 259.41 | 0.24 |
|   | 0.93 | 734.00 | 0.45 | 333.53 | 0.42 |
|   | 0.89 | 833.59 | 0.43 | 362.70 | 2.00 |
| B | 0.91 | 749.82 | 0.44 | 335.59 | 0.64 |
|   | 1.09 | 462.80 | 0.46 | 217.39 | 0.09 |
|   | 0.96 | 572.44 | 0.45 | 258.89 | 0.38 |
|   | 0.90 | 788.76 | 0.44 | 351.24 | 1.53 |
| C | 1.20 | 353.90 | — | — | — |
|   | 1.02 | 539.70 | — | — | — |
|   | 0.93 | 712.67 | 0.42 | 305.81 | 1.00 |
|   | 0.94 | 711.10 | 0.42 | 305.81 | 1.00 |
|   | 0.88 | 934.30 | — | — | — |
| D | 1.28 | 237.30 | — | — | — |
|   | 1.10 | 413.90 | — | — | — |
|   | 0.95 | 606.60 | 0.41 | 247.27 | 0.30 |
|   | 0.96 | 636.60 | 0.41 | 259.45 | 0.30 |
|   | 0.89 | 866.20 | — | — | — |
| E | 1.17 | 316.70 | — | — | — |
|   | 1.01 | 477.10 | 0.33 | 158.57 | 0.01 |
|   | 1.01 | 453.26 | 0.33 | 150.66 | 0.01 |
|   | 0.92 | 673.50 | — | — | — |
| F | 1.30 | 242.80 | — | — | — |
|   | 1.09 | 416.60 | — | — | — |
|   | 0.96 | 661.20 | 0.39 | 256.80 | 0.07 |
|   | 0.96 | 679.42 | 0.39 | 263.85 | 0.07 |
|   | 0.89 | 848.70 | — | — | — |
| G | 0.99 | 502.07 | 0.37 | 186.35 | 0.04 |
|   | 0.93 | 605.73 | 0.36 | 216.58 | 0.04 |
|   | 1.47 | 144.58 | — | — | — |
|   | 1.25 | 319.48 | — | — | — |
|   | 1.08 | 410.12 | — | — | — |
|   | 0.98 | 563.39 | — | — | — |

TABLE II-continued

| Feed | H-to-C ratio of liquid product | UV$_{prod}$ | Y$_{liq}$ | UV$_{corr}$ | Coking Rate (mm/day) |
|---|---|---|---|---|---|
| H | 1.12 | 432.74 | — | — | — |
|   | 0.96 | 599.95 | — | — | — |
|   | 0.90 | 784.02 | — | — | — |
|   | 0.87 | 917.98 | — | — | — |
| I | 1.50 | 107.80 | — | — | — |
|   | 1.20 | 306.50 | — | — | — |
|   | 1.02 | 489.70 | — | — | — |
|   | 0.91 | 776.80 | — | — | — |
| J | 1.18 | 256.90 | — | — | — |
|   | 0.99 | 499.80 | — | — | — |
|   | 0.93 | 702.70 | — | — | — |

EXAMPLE 3

(Illustrative)

From the data and analysis set out in Example 1 above, it will be appreciated that ultra-violet analysis provides a very suitable and convenient means for monitoring and controlling a hydrocarbon thermal cracking process preparing olefins. A typical process scheme incorporating the analysis described in Example 1 would be as follows.

Natural gasoline (30,000 kg/hr) is mixed with steam (steam-to-hydrocarbon weight ratio of 0.55) and fed to a thermal cracking unit. The thermal cracking unit operates with a coil outlet temperature of about 800° C. and a coil outlet pressure of about 2 bar. The hydrocarbon has a residence time of 0.3 seconds in the thermal cracking unit.

The effluent from the thermal cracking unit is fed to a separation unit. For the first stage of separation, the effluent is quenched to yield a light hydrocarbon gas fraction and a liquid hydrocarbon fraction. A sample of the liquid fraction is removed and fed to an UV absorption analyzer, in which absorption by the sample of ultra-violet light in the 310 to 550 nm wavelength range is determined. The UV absorption analyzer generates a signal which is fed to a controller. The controller compares the signal with a present signal value. Differences between the signal generated by the UV absorption analyzer and the preset signal cause the controller to adjust the operating temperature or hydrocarbon flowrate of the thermal cracking unit. This has the effect of adjusting the cracking severity of the thermal cracking unit.

The gaseous fraction comprising $C_4$ hydrocarbons leaving the quench unit is separated by means of successive compression and distillation operations into the desired products. The process yields 9,000 kg/hr ethylene (30% yield on gasoline) at maximum cracking severity (equivalent to a hydrogen-to-carbon ratio in the effluent liquid fraction of 1.1). The yield of ethylene when using a traditional thermal cracking unit control system reliant on determining the propylene-to-methane ratio (PMR) of the effluent would be 8100 kg/hr. It can thus be seen that controlling the thermal cracking unit by using UV absorption analysis to monitor the hydrogen-to-carbon ratio in the liquid effluent can give significant increase in ethylene yield.

What is claimed is:

1. A method for determining the hydrogen-to-carbon ratio of a liquid hydrocarbon fraction, which method comprises subjecting a sample of a liquid hydrocarbon fraction to an ultra-violet absorption analysis and, using a predetermined correlation between the ultra-violet absorbance and the hydrogen-to-carbon ratio of like hydrocarbon fractions, determining the hydrogen-to-carbon ratio of the said liquid hydrocarbon fraction.

2. A method according to claim 1, wherein the analysis determines the absorbance of ultra-violet light at a wavelength of 310 nm and greater.

3. A method according to claim 2, wherein the analysis determines the absorbance of ultra-violet light at a wavelength of from 310 to 550 nm.

4. A method according to claim 1, wherein the liquid hydrocarbon fraction is the liquid product of a hydrocarbon thermal cracking process.

5. A process for the preparation of olefins by the thermal cracking of a hydrocarbon feedstock, which process comprises the steps of (a) feeding a hydrocarbon feedstock to a thermal cracking zone and subjecting the hydrocarbon feedstock to operating conditions under which at least a portion of the hydrocarbon feedstock is thermally cracked, thereby yielding a cracking product;

(b) recovering from the cracking product a liquid hydrocarbon fraction;

(c) subjecting the liquid hydrocarbon fraction to an analysis in which the ultra-violet absorbance of the liquid hydrocarbon fraction is determined yielding an analytical result which may be correlated to the hydrogen-to-carbon ratio of the liquid hydrocarbon fraction;

(d) comparing the analytical result with a predetermined desired analytical result correlating to a desired hydrogen-to-carbon ratio in the liquid hydrocarbon fraction, wherein the desired hydrogen-to-carbon ratio correlates to a desired olefin product; and (e) adjusting the operating conditions of the cracking zone to obtain the desired analytical result.

6. A process according to claim 5, wherein the hydrocarbon feedstock is selected from the group consisting of gasoline, naphtha, kerosine and heavy gasoils.

7. A process according to claim 5, wherein the analysis determines the absorbance of ultra-violet light at a wavelength of 310 nm and greater.

8. A process according to claim 7, wherein the analysis determines the absorbance of ultra-violet light at a wavelength of from 310 to 550 nm.

9. A method for controlling a process for the thermal cracking of a hydrocarbon feedstock in a thermal cracking zone, which method comprises recovering a sample of a liquid hydrocarbon fraction of a cracking product obtained from the thermal cracking of a hydrocarbon feedstock in a thermal cracking zone; subjecting the sample to an analysis in which the ultra-violet absorbance of the sample is determined yielding an analytical result which may be correlated to the hydrogen-to-carbon ratio of the liquid hydrocarbon fraction; comparing the analytical result with a predetermined desired analytical result correlating to a desired hydrogen-to-carbon ratio in the liquid hydrocarbon fraction; and adjusting the operating conditions of the cracking zone to obtain the desired analytical result.

10. A method according to claim 9, wherein the analysis determines the absorbance of ultra-violet light at a wavelength of 310 nm and greater.

11. A method according to claim 10, wherein the analysis determines the absorbance of ultra-violet light at a wavelength of from 310 to 550 nm.

12. A method according to claim 9, wherein the hydrocarbon feedstock is selected from the group consisting of gasoline, naphtha, kerosine and heavy gasoils.

13. A method for monitoring the quench coking rate in a process for the preparation of olefins by the thermal cracking of a hydrocarbon feedstock, which method comprises the steps of:

(a) subjecting a sample of a hydrocarbon feedstock to an analysis in which the ultra-violet absorbance of the hydrocarbon feedstock is determined yielding a first analytical result, $UV_{feed}$, correlating to a hydrogen-to-carbon ratio of the hydrocarbon feedstock;

(b) feeding the hydrocarbon feedstock to a thermal cracking zone and subjecting the hydrocarbon feedstock to operating conditions under which at least a portion of the hydrocarbon feedstock is thermally cracked, thereby yielding a cracking product;

(c) recovering from the cracking product a liquid hydrocarbon fraction;

(d) measuring the yield of liquid hydrocarbons, $Y_{liq}$, obtained;

(e) subjecting a sample of the liquid hydrocarbon fraction to an analysis in which the ultra-violet absorbance of the liquid hydrocarbon fraction is determined yielding a second analytical result, $UV_{prod}$, correlating to a hydrogen-to-carbon ratio of the liquid hydrocarbon fraction;

(f) correcting the second analytical result for effects of the hydrocarbon feedstock and the yield of liquid hydrocarbons to yield a corrected analytical result, $UV_{corr}$, wherein $$UV_{corr} = UV_{feed} + Y_{liq}(UV_{prod} - UV_{feed}); \text{ and}$$

(g) determining the coking rate from the corrected analytical result, wherein $$ln(\text{coking rate}) = R + S(ln\ UV_{corr}),$$

where R and S are constants.

14. A method according to claim 13, wherein the analysis determines the absorbance of ultra-violet light at a wavelength of 310 nm and greater.

15. A method according to claim 14, wherein the analysis determines the absorbance of ultra-violet light at a wavelength of from 310 to 550 nm.

16. A method according to claim 13, wherein the hydrocarbon feedstock is selected from the group consisting of gasoline, naphtha and kerosine.

* * * * *